United States Patent
Gerasopoulos et al.

(10) Patent No.: US 11,786,153 B2
(45) Date of Patent: Oct. 17, 2023

(54) WEARABLE SENSOR

(71) Applicant: The Johns Hopkins University, Baltimore, MD (US)

(72) Inventors: Konstantinos Gerasopoulos, Odenton, MD (US); Julia B. Patrone, Ellicott City, MD (US); Leslie H. Hamilton, Silver Spring, MD (US); Luke J. Currano, Columbia, MD (US); Matthew A. Hagedon, Columbia, MD (US); Felix Connor Sage, Ijamsville, MD (US); Mekbib Astatke, Gaithersburg, MD (US)

(73) Assignee: The Johns Hopkins University, Baltimore, MD (US)

( * ) Notice: Subject to any disclaimer, the term of this patent is extended or adjusted under 35 U.S.C. 154(b) by 69 days.

(21) Appl. No.: 16/556,540

(22) Filed: Aug. 30, 2019

(65) Prior Publication Data
US 2020/0138343 A1    May 7, 2020

Related U.S. Application Data

(60) Provisional application No. 62/754,603, filed on Nov. 2, 2018.

(51) Int. Cl.
*A61B 5/1486*    (2006.01)
*A61B 5/00*    (2006.01)
(Continued)

(52) U.S. Cl.
CPC .......... *A61B 5/1486* (2013.01); *A61B 5/0002* (2013.01); *A61B 5/14517* (2013.01);
(Continued)

(58) Field of Classification Search
CPC ... A61B 5/1486; A61B 5/6833; A61B 5/4266; A61B 5/14532; A61B 5/14517;
(Continued)

(56) References Cited

U.S. PATENT DOCUMENTS 8,168,051 B2 * 5/2012 Say .................... G01N 27/3272
204/403.01
2003/0023317 A1 * 1/2003 Brauker ................ A61B 5/076
623/23.76
(Continued)

OTHER PUBLICATIONS

Ji, X. et al. (Aug. 2016). "Highly sensitive metabolite biosensor based on organic electrochemical transistor integrated with microfluidic channel and poly(N-vinyl-2-pyrrolidone)-capped platinum nanoparticles". Advanced Materials Technologies, (Year: 2016).*
(Continued)

*Primary Examiner* — Christian Jang
(74) *Attorney, Agent, or Firm* — Todd R. Farnsworth

(57) ABSTRACT

A wearable sensor system includes a flexible patch, an electronic circuit disposed on the flexible patch, and a disposable sensor disposed on the flexible patch and connected to the electronic circuit via a socket. The disposable sensor detects a chemical compound. The electronic circuit generates a detection signal commensurate with the chemical compound detected by the disposable sensor. The disposable sensor is removably plugged into the socket, thereby permitting replacement of the disposable sensor upon satisfaction of a predetermined condition. A battery disposed is on the flexible patch and connected to the electronic circuit to power the electronic circuit. A transceiver is connected to the electronic circuit, wherein the transceiver transmits the detection signal.

16 Claims, 4 Drawing Sheets

(51) Int. Cl.
A61B 5/145 (2006.01)
A61B 5/1477 (2006.01)
(52) U.S. Cl.
CPC ...... *A61B 5/14532* (2013.01); *A61B 5/14546* (2013.01); *A61B 5/4266* (2013.01); *A61B 5/685* (2013.01); *A61B 5/6833* (2013.01); *A61B 5/1477* (2013.01); *A61B 2560/0214* (2013.01)
(58) Field of Classification Search
CPC ... A61B 5/685; A61B 5/0002; A61B 5/14546; A61B 5/1477; A61B 2560/0214; A61B 5/6832; A61B 5/14514; A61B 5/1451; A61B 5/14507; A61B 5/00; A61B 5/0026; A61B 5/0015; A61B 5/0004; A61B 5/1482
See application file for complete search history.

(56) References Cited

U.S. PATENT DOCUMENTS

| | | | | |
|---|---|---|---|---|
| 2004/0225199 | A1* | 11/2004 | Evanyk | A61B 5/0002 128/903 |
| 2009/0084678 | A1* | 4/2009 | Joshi | A61B 5/14865 204/403.14 |
| 2009/0143658 | A1* | 6/2009 | Petisce | A61B 5/14532 204/403.11 |
| 2009/0198117 | A1* | 8/2009 | Cooper | A61B 5/6846 600/347 |
| 2014/0135605 | A1* | 5/2014 | Gottlieb | A61B 5/742 600/347 |
| 2016/0374585 | A1* | 12/2016 | Fonash | A61B 5/053 600/547 |
| 2017/0027481 | A1* | 2/2017 | Coppede' | A61B 5/1486 |
| 2019/0046780 | A1* | 2/2019 | Thomas | A61M 5/14248 |
| 2019/0110722 | A1* | 4/2019 | Ionescu | B01L 3/502715 |

OTHER PUBLICATIONS

Huang, X. et al., Stretchable, Wireless Sensors and Functional Substrates for Epidermal Characterization of Sweat, Small 10, 2014, 3083-3090.
Jang, K.I. et al., Rugged and breathable forms of stretchable electronics with adherent composite substrates for transcutaneous monitoring, Nat. Commun. 5, ncomms5779, 2014.
Kim, D. H. et al., Epidermal Electronics, Science 333, 2011, 838-843.
Kim, J. et al., Miniaturized Battery-Free Wireless Systems for Wearable Pulse Oximetry. Adv. Funct. Mater. 27, 2017.
Lochner, C. M. et al., All-organic optoelectronic sensor for pulse oximetry. Nat. Commun. 5, ncomms6745, 2014.
Yeo, W. H. et al., Multifunctional Epidermal Electronics Printed Directly Onto the Skin. Adv. Mater. 25, 2013, 2773-2778.
Rose, D. P. et al., Adhesive RFID Sensor Patch for Monitoring of Sweat Electrolytes. IEEE Trans. Biomed. Eng. 62, 2015, 1457-1465.
Sonner, Z. et al., The microfluidics of the eccrine sweat gland, including biomarker partitioning, transport, and biosensing implications. Biomicrofluidics 9, 031301, 2015.
Bandodkar, A. J. et al., J. Tattoo-Based Wearable Electrochemical Devices: A Review. Electroanalysis 27, 2015, 562-572.
Glennon, T. et al., 'SWEATCH': A Wearable Platform for Harvesting and Analysing Sweat Sodium Content. Electroanalysis 28, 2016, 1283-1289.
Guinovart, T., J. et al., A potentiometric tattoo sensor for monitoring ammonium in sweat. Analyst 138, 2013, 7031-7038.
Jia, W. et al., Electrochemical Tattoo Biosensors for Real-Time Noninvasive Lactate Monitoring in Human Perspiration. Anal. Chem. 85, 2013, 6553-6560.
Kim, J. et al., Wearable temporary tattoo sensor for real-time trace metal monitoring in human sweat. Electrochem. Commun. 51, 2015, 41-45.
Kim, J. et al., Noninvasive Alcohol Monitoring Using a Wearable Tattoo-Based Iontophoretic-Biosensing System. ACS Sens. 1, 2016, 1011-1019.
Gao, W. et al., Fully integrated wearable sensor arrays for multiplexed in situ perspiration analysis. Nature 529, 2016, 509-514.
Imani, S. et al., A wearable chemical-electrophysiological hybrid biosensing system for real-time health and fitness monitoring. Nat. Commun. 7, ncomms11650, 2016.
Lee, H. et al., A graphene-based electrochemical device with thermoresponsive microneedles for diabetes monitoring and therapy, Nat. Nanotechnol. 11, 2016, 566-572.
Bandodkar, A. J. et al., Wearable Chemical Sensors: Present Challenges and Future Prospects, ACS Sens. 1, 2016, 464-482.
Bandodkar, A. J. et al., Non-invasive wearable electrochemical sensors: a review, Trends Biotechnol. 32, 2014, 363-371.
Windmiller, J. R. et al., Wearable Electrochemical Sensors and Biosensors: A Review. Electroanalysis 25, 2013, 29-46.
Bandodkar, A. J. et al. Epidermal tattoo potentiometric sodium sensors with wireless signal transduction for continuous non-invasive sweat monitoring, Biosens. Bioelectron. 54, 2014, 603-609.
Lee, J. W. et al., Soft, thin skin-mounted power management systems and their use in wireless thermography, Proc. Natl. Acad. Sci. U. S. A. 113, 2016, 6131-6136.
Arya, K. S. et al., Antibody functionalized interdigitated .MU.-electrode (ID.MU.E) based impedimetric cortisol biosensor. Analyst 135, 2010, 1941-1946.
Sun, K. et al., An immunoelectrochemical sensor for salivary cortisol measurement, Sens. Actuators B Chem. 133, 2008, 533-537.
Suo, L. et al., 'Water-in-salt' electrolyte enables high-voltage aqueous lithium-ion chemistries, Science 350, 2015, 938-943.
Khodagholy, D. et al., High transconductance organic electrochemical transistors, Nat. Commun. 4, 2013.
Ji, X. et al., Highly Sensitive Metabolite Biosensor Based on Organic Electrochemical Transistor Integrated with Microfluidic Channel and Poly(N-vinyl-2-pyrrolidone)-Capped Platinum Nanoparticles, Adv. Mater. Technol. 1, 2016.
Kim, D. J. et al., Organic electrochemical transistor based immunosensor for prostate specific antigen (PSA) detection using gold nanoparticles for signal amplification, Biosens. Bioelectron. 25, 2010, 2477-2482.
Liao, C. et al., Highly selective and sensitive glucose sensors based on organic electrochemical transistors with graphene-modified gate electrodes, J. Mater. Chem. B 1, 2013, 3820-3829.
Mak, C. H. et al., Highly-sensitive epinephrine sensors based on organic electrochemical transistors with carbon nanomaterial modified gate electrodes, J. Mater. Chem. C 3, 2015, 6532-6538.
Shim, N. Y. et al., All-Plastic Electrochemical Transistor for Glucose Sensing Using a Ferrocene Mediator, Sensors 9, 2009, 9896-9902.
Tang, H. et al., Highly Sensitive Glucose Biosensors Based on Organic Electrochemical Transistors Using Platinum Gate Electrodes Modified with Enzyme and Nanomaterials, Adv. Funct. Mater. 21, 2011, 2264-2272.
Derbyshire, P. J. et al., Lactate in human sweat: a critical review of research to the present day, J. Physiol. Sci. JPS 62, 2012, 429-440.
Rassaei, L. et al., A. Lactate biosensors: current status and outlook, Anal. Bioanal. Chem. 406, 2014, 123-137.
Long, B. et al., Ready for Prime Time? Biomarkers in Sepsis, Emerg. Med. Clin. North Am. 35, 2017, 109-122.
Fan, S. L. et al., Diagnosing sepsis—The role of laboratory medicine, Clin. Chim. Acta 460, 2016, 203-210.
Yang, S. Y. et al., Organic Electrochemical Transistors for Sensor Applications, Iontronics: Ionic Carriers in Organic Electronic Materials and Devices, 2011, p. 166, CRC Press.
Karyakin, A. A. et al., On the mechanism of H2O2 reduction at Prussian Blue modified electrodes, Electrochem. Commun. 1, 1999, 78-82.

(56) References Cited

OTHER PUBLICATIONS

Katsounaros, I. et al., Hydrogen peroxide electrochemistry on platinum: towards understanding the oxygen reduction reaction mechanism, Phys. Chem. Chem. Phys. 14, 2012, 7384-7391.

Kergoat, L. et al., Detection of Glutamate and Acetylcholine with Organic Electrochemical Transistors Based on Conducting Polymer/ Platinum Nanoparticle Composites, Adv. Mater. 26, 2014, 5658-5664.

Michaelis et al., Die Kinetik der invertinwirkung. Biochem Z 49, 1913, 33-367 (English Translation).

Marasovic et al., Robust Nonlinear Regression in Enzyme Kinetic Parameters Estimation, Journal of Chemistry, 2017.

* cited by examiner

WEARABLE SENSOR

CROSS-REFERENCE TO RELATED APPLICATION(S)

This application claims the benefit of U.S. Provisional Application No. 62/754,603, filed Nov. 2, 2018, the entire content of which is hereby incorporated by reference.

FIELD OF THE INVENTION

The disclosure relates generally to wearable sensors. More particularly, the present invention concerns wearable sensors for detecting biological molecules (also referred to as "biomarkers") in a user's perspiration or skin.

DESCRIPTION OF THE RELATED ART

The prior art describes a number of wearable sensors. Those sensors, however, suffer from a number of deficiencies.

In particular, wearable sensors typically are not light in weight, because they are made from materials that are bulky and/or heavy.

In addition, existing wearable sensors have typically been made from rigid, inflexible materials. This has limited the form factors for commercial wearable sensors to watches, bracelets, chest bands, and similar articles that require a fastening strap to encircle part of the body. A less obtrusive form factor is desired.

While there is growing body of research on sensing patches that adhere to the skin in a manner similar to a temporary tattoo, these are challenging to manufacture, and it is difficult to incorporate a battery because large, rigid pieces do not integrate well with the super-flexible films. Therefore, many of these devices only sense and log data when a wireless power source is brought in close proximity to the sensor, which can lead to sporadic rather than continuous data.

Further, prior art sensors designed as patches typically have limited lifetime owing to the fact that they are ultra-thin and are glued to the skin. As the dead skin cells on the surface of the skin slough off, the sensor patch will disintegrate and peel off in the same manner as a temporary tattoo.

SUMMARY OF THE INVENTION

In view of the foregoing, a desire has arisen for a wearable sensor that addresses some of the deficiencies identified herein.

The present invention provides for a flexible form factor while retaining a conventional, low cost manufacturing process based on flexible printed circuit board manufacturing. This is amenable to integration of thin film batteries as well as conventional packaged integrated circuits.

The present invention also incorporates a re-usable adhesive that allows for removal and reattachment of the sensor as desired.

Still further, the invention incorporates a replaceable sensor that allows for re-use of the electronics while replacing the sensor with a new sensor element. The ability to replace the sensor element is needed for some types of chemical sensors, as the active parts of the sensor may age, degrade, or be consumed during normal operation.

Replaceability also allows for switching between different types of sensors, for instance switching between sensors designed to measure different biomarkers, while making the electronics reusable allows for cost-effective implementation.

In view of the foregoing, the present invention provides for a wearable sensor system that includes a flexible patch, an electronic circuit disposed on the flexible patch, and a disposable sensor disposed on the flexible patch and connected to the electronic circuit via a socket. The disposable sensor detects a chemical compound. The electronic circuit generates a detection signal commensurate with the chemical compound detected by the disposable sensor. The disposable sensor is removably plugged into the socket, thereby permitting replacement of the disposable sensor upon satisfaction of a predetermined condition. A battery is disposed on the flexible patch and connected to the electronic circuit to power the electronic circuit. A transceiver is connected to the electronic circuit, wherein the transceiver transmits the detection signal.

In one contemplated embodiment, the wearable sensor system also includes an adhesive disposed on the flexible patch to affix the flexible patch to a skin of a user.

While variants may be employed, the disposable sensor is contemplated to be a thin film transistor, such as an organic electrochemical transistor ("OECT").

In another contemplated embodiment of the wearable sensor system, the disposable sensor includes a substrate, a gate electrode disposed on the substrate, a source drain electrode disposed on the substrate, an immobilizing matrix disposed on the gate electrode, and an enzyme immobilized within the immobilizing matrix. The enzyme is selected to react with a biological molecule to produce the chemical compound detectible by the disposable sensor.

The disposable sensor may detect the chemical compound from perspiration of the user.

In an embodiment of the wearable sensor system, the gate electrode includes a first conductive layer disposed on the substrate and a second conductive layer disposed atop the first conductive layer. Here, the first conductive layer may be gold and the second conductive layer may be platinum and/or ferric ferrocyanide (also referred to as Prussian blue).

Without limiting the invention, it is contemplated that the gate electrode and the source drain electrode are parallel to one another.

It is also contemplated that the gate electrode and the source drain electrode will be separated from one another by a predetermined distance.

Also, the enzyme is contemplated to be selected to react with one or more biomarkers of: lactate, glucose, glutamate, and acetylcholine. As such, the enzyme may be lactate oxidase when the biological molecule is lactate; glucose oxidase when the biological molecule is glucose; 2-oxoglutarate when the biological molecule is glutamate; or acetylcholine esterase and choline oxidase when the biological molecule is acetylcholine.

In another embodiment, the immobilizing matrix includes bovine serum albumin and glutaraldehyde.

The wearable sensor system also may include a mechanism providing access to an electrolyte to fluidically connect the gate electrode to the source drain electrode. The electrolyte at least partially includes the perspiration of the user.

Still further, the wearable sensor system may include an array of microneedles as the mechanism providing access to the electrolyte.

Concerning the disposable sensor, in one embodiment it is contemplated that the component will include at least one three electrode cell. The three electrode cell may include a substrate, a working electrode disposed on the substrate, a reference electrode disposed on the substrate, a counter electrode disposed on the substrate, an immobilizing matrix disposed on the working electrode, and an enzyme immobilized within the immobilizing matrix. As before, the enzyme is contemplated to be selected to react with a biological molecule to produce the chemical compound detectible by the disposable sensor.

The disposable sensor is contemplated to detect a concentration of the chemical compound.

In an embodiment, the disposable sensor detects a concentration of the chemical compound at a periodic interval.

The chemical compound detected by the disposable sensor may be hydrogen peroxide.

The detection signal is contemplated to provide information concerning a concentration of the chemical compound.

The transceiver is contemplated to transmit the detection signal wirelessly.

Further details of these and other aspects of the subject matter of the present invention will be apparent from the detailed description and drawings included below.

BRIEF DESCRIPTION OF THE DRAWINGS

Reference is now made to the accompanying drawings, in which.

DETAILED DESCRIPTION OF EMBODIMENT(S) OF THE INVENTION

One or more embodiments are described in connection with the present invention. The embodiments are intended to illustrate the breadth and scope of the present invention rather than to limit the scope thereof.

Figure 1:
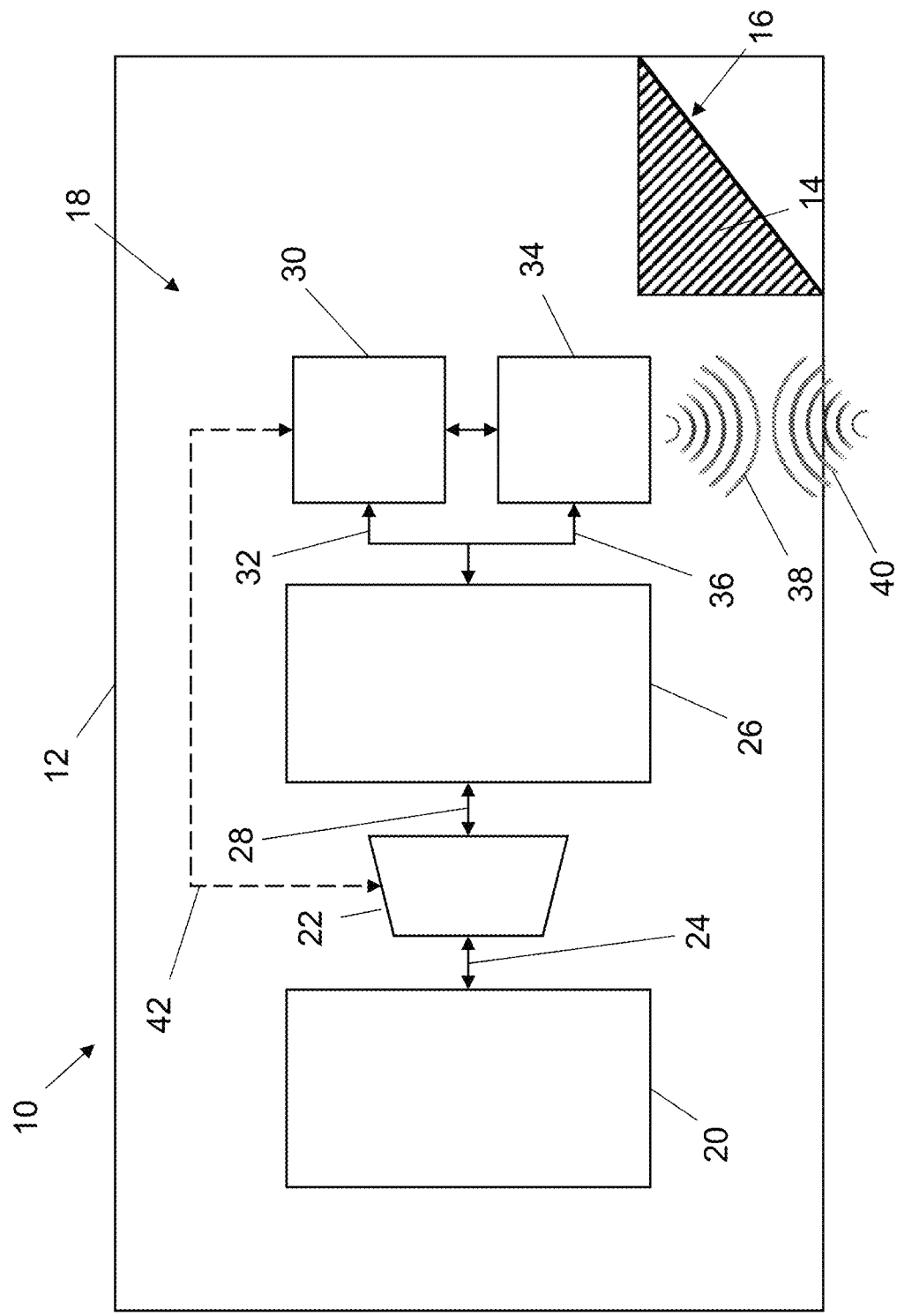
FIG. 1 is a graphical illustration of a first contemplated embodiment of a wearable sensor system according to the present invention.

FIG. 1 is a graphical representation of a generic example of the wearable sensor system 10 of the present invention.

The wearable sensor system 10 is intended to be worn on or against the skin of a user. As detailed in the paragraphs that follow, the wearable sensor system 10 is provided with features and components permitting the wearable sensor system 10 to detect at least one biological material, biological molecule, or biomarker in the perspiration of the user.

For simplicity, the discussion that follows refers to the detection of a biological molecule in a user's perspiration. It is noted, however, that the present invention is not limited to a wearable sensor system 10 that detects only one type of specific biological molecule, or to perspiration as the source of biological molecules. The wearable sensor system 10 of the present invention may be adapted to detect two or more types of biological molecules, as should be apparent to those skilled in the art.

To simplify the discussion that follows, one biological molecule that is contemplated to be detected by the wearable sensor system 10 of the present invention is lactate in the user's perspiration. For clarity, the present invention is not intended to be limited solely to the detection of lactate in perspiration. The present invention may be employed to detect the presence of any number of biological molecules in perspiration or on a user's skin. Accordingly, the discussion of the wearable sensor system 10 of the present invention is intended to encompass these variations as if described herein.

Separately, those skilled in the art easily may employ the wearable sensor system 10 of the present invention to detect biological molecules in fluids other than a user's perspiration. Other fluids include, but are not limited to, blood, tears, saliva, interstitial fluid, etc. Any such variations also are intended to be encompassed by the scope of the present invention.

In that the wearable sensor system 10 of the present invention is contemplated to be worn on the skin of a user, the wearable sensor system 10 is contemplated to be made as a flexible patch 12. The flexible patch 12 is contemplated to adhere to the user's skin. So that the flexible patch 12 adheres to the user's skin, one side of the flexible patch 12 is contemplated to be provided with an adhesive 14.

Separately, it is contemplated that the wearable sensor system 10 may be incorporated into a wearable item. For example, the wearable sensor system 10 may be incorporated into a bracelet, strap, or wrist band.

In another contemplated embodiment, the wearable sensor system 10 may be incorporated into an elastic fabric so that the wearable sensor system 10 may be pressed against the user's skin. Contemplated elastic fabrics include, but are not limited to, elastic waistbands, socks, shirts, compression shorts, compression shirts, and the like. As should be apparent, if the wearable sensor system 10 is incorporated into or attached to an elastic fabric, it is not likely that the wearable sensor system 10 will include the adhesive 14.

The flexible patch 12 may be made from any of a number of materials. In one contemplated embodiment, the flexible patch may be made from KAPTON™ film. "KAPTON" is recognized as a trademark for a material developed by E.I. DuPont de Nemours & Co that may be used, inter alia, for flexible printed circuits. The generic chemical name for KAPTON is poly(4,4'-oxydiphenylene-pyromellitimide).

While poly(4,4'-oxydiphenylene-pyromellitimide) is contemplated as one material that may be used to construct the flexible patch 12, other materials may be employed in the alternative, as should be apparent to those skilled in the art.

The material used for the flexible patch 12 is contemplated to be a non-woven film. However, the flexible patch 12 may be constructed from a woven material without departing from the scope of the present invention.

As noted, the flexible patch 12 is contemplated to be made from a material that is "flexible." While not intended to limit the scope of the present invention, a flexible material is contemplated to be a material that conforms to the contours of a user's skin, wherever the flexible patch 12 may be adhered on the user's body. A flexible material also is contemplated to be a material that conforms to changes in the contours of a user's skin when the user moves his or her body.

It is contemplated that the size of the flexible patch 12 is likely to have an impact on the degree of flexibility of the material employed therefor. In particular, the larger the surface area of the flexible patch 12, the greater the need for the flexible patch 12 to be made from a flexible material. However, if the flexible patch 12 is made to have a small surface area, it is contemplated that the material comprising the flexible patch 12 may be less flexible while exhibiting suitable properties for comfort and wear. It is contemplated that those skilled in the art will appreciate the interplay between the degree of flexibility of the flexible patch 12 and the size of the patch. Accordingly, a wide range for the degree of flexibility of the flexible patch 12 is contemplated to fall within the scope of the present invention. Also, the flexible patch 12 may be constructed in any number of sizes without departing from the scope of the present invention.

FIG. 1 illustrates the flexible patch 12 as rectangularly-shaped. As should be apparent from the instant description, the present invention is not intended to be limited to a rectangular shape. For example, the flexible patch 12 may be triangular, trapezoidal, square, circular, elliptical, or amorphously-shaped without departing from the scope of the present invention.

As noted above, the flexible patch 12 is contemplated to comprise an adhesive 14 to affix the flexible patch 12 to a user's skin. As illustrated in FIG. 1, the adhesive 14 is shown as being applied to the bottom side 16 of the flexible patch 12, while other components of the wearable sensor system 10 are disposed on the top side 18 of the flexible patch 12. In an alternative, it is contemplated that at least some or all of the components, which are discussed in greater detail below, may be included on the bottom side 16 with the adhesive 14.

The adhesive 14 may be of any type suitable to affix the flexible patch 12 to the user's skin. The adhesive 14 may be any type of adhesive commonly referred to as medical adhesive, bandage adhesive, or the like. Furthermore, the adhesive 14 may be selected so that the flexible patch 12 may be removed from the user's skin and reattached thereto. As should be apparent to those skilled in the art, there are a wide variety of suitable adhesives may be employed without departing from the scope of the present invention.

It is contemplated that the adhesive 14 will cover the entire bottom surface 16 of the flexible patch 12. However, this is not necessary to practice the present invention. The adhesive 14 may be applied to any fractional portion of the bottom surface 16 while continuing to provide adhesion suitable to achieve the objectives of the present invention.

As shown in FIG. 1, the top surface 18 of the flexible patch 12 includes several components. In particular, a disposable sensor 20 is disposed on the top surface 18 of the flexible patch 12. The disposable sensor 20 plugs into a socket 22 via a first connection 24. The socket 22, in turn, is connected to an electronic circuit 26 via a second connection 28. The electronic circuit 26 connects to a battery 30 via a third connection 32. The electronic circuit 26 also connects to a transceiver 34 via a fourth connection 36. The transceiver 34 may transmit first signals 38 and receive second signals 40.

The disposable sensor 20, embodiments of which are described in greater detail herein, is capable of detecting one or more biological molecules, either directly or indirectly. As such, the disposable sensor 20 may have any number of constructions consistent with the biological molecules to be detected. The construction of the disposable sensor 20 should be apparent to those skilled in the art.

In one example, the disposable sensor 20 is a thin film transistor such as an organic electrochemical transistor ("OECT"). Some contemplated alternatives to an OECT are a three electrode electrochemical cell, a surface acoustic wave sensor, a microelectromechanical capacitive sensor such as a cantilever, and the like, the details of all of which should be apparent to those skilled in the art.

While FIG. 1 illustrates a single disposable sensor 20, the present invention should not be understood to be limited to a construction having only one disposable sensor 20. In an alternative construction, it is contemplated that two or more disposable sensors 20 may be attached to the top surface 16 of the flexible patch 12 without departing from the scope of the present invention.

As illustrated, the disposable sensor 20 connects to the electronic circuit 26 via a socket 22, via the first connection 24, and via the second connection 28. As noted above, an OECT is one non-limiting example of a disposable sensor 20 that may be employed by the wearable sensor system 10 according to the present invention.

The disposable sensor 20 is referred to as being "disposable" for at least one reason. It is contemplated that the disposable sensor 20, regardless of the biological molecules detected, may include a consumable material (e.g., an enzyme or a catalyst) that reacts with the biological molecules. The consumable material may be, alternatively, a material that is subject to saturation. As such, when the consumable material is depleted and/or saturated, the used disposable sensor 20 needs to be replaced with a new disposable sensor 20. The depletion and/or saturation of the disposable sensor 20 is a predetermined condition that, when satisfied, requires replacement of the disposable sensor 20.

The socket 22 is contemplated to be a connector into which the disposable sensor 20 may be plugged and from which it may be unplugged to facilitate replacement of the disposable sensor 20 upon satisfaction of the predetermined condition (e.g., that the disposable sensor 20 is "used"). Alternatively, the socket 22 may be used to connect to a second disposable sensor 20 that detects a different biomarker than a first disposable sensor 20.

Examples of the socket 22 include, but are not limited to pin connectors, magnetic connectors, adhesive connectors, and the like, as well as connectors commonly used in printed circuits, such as flexible printed circuit connectors or flexible flat cable connectors.

As should be apparent, it is possible that the disposable sensor 20 may not employ a consumable material. If so, the wearable sensor system 10 need not incorporate a disposable sensor 20. The present invention is intended to encompass this embodiment as well.

Concerning the first connection 24 and the second connection 28, any suitable construction may be employed as should be apparent to those skilled in the art. In the illustrated embodiment, the first connection 24 and the second connection 28 are contemplated to be hardwired connections.

A hardwired connection may include, inter alia, the socket 22 discussed above and, therefore, the hardwired connection should not be understood to be a permanent connection. Semi-permanent connections, like the socket 22, are contemplated to fall within the scope of the present invention.

Separately, wireless connections may be employed, as required or as desired.

In the illustrated embodiment, the disposable sensor 20 receives power from the battery 30 through the electronic circuit 26. Alternatively, power may be provided to the disposable sensor 20 from the battery 30 through a fifth connection 42, which is shown in dotted line format in FIG. 1.

The electronic circuit 26 receives power from the battery 30 via the third connection 32. As should be apparent to those skilled in the art, this direct connection to the battery 30 is not required to practice the present invention. Other connections are possible, and those other connection possibilities are contemplated to fall within the scope of the present invention.

The battery 30 may be a thin, low-profile rechargeable battery as described in, for example, U.S. application Ser.

No. 16/054,282, entitled "Gel Polymer Electrolyte Compositions and Electrochemical Cells Including the Same," filed on Aug. 3, 2018, and published as U.S. Patent Application Publication No. 2019/0237803. The content of U.S. application Ser. No. 16/054,282 is hereby incorporated by reference in its entirety.

The electronic circuit 26 is contemplated to encompass any number of components that are required and/or desired for operation of the wearable sensor system 10 of the present invention. Regardless of its construction, the electronic circuit 26 is contemplated to cooperate with the disposable sensor 20 to generate a detection signal commensurate with the presence of the biological molecules detected by the disposable sensor 20.

Figure 4:
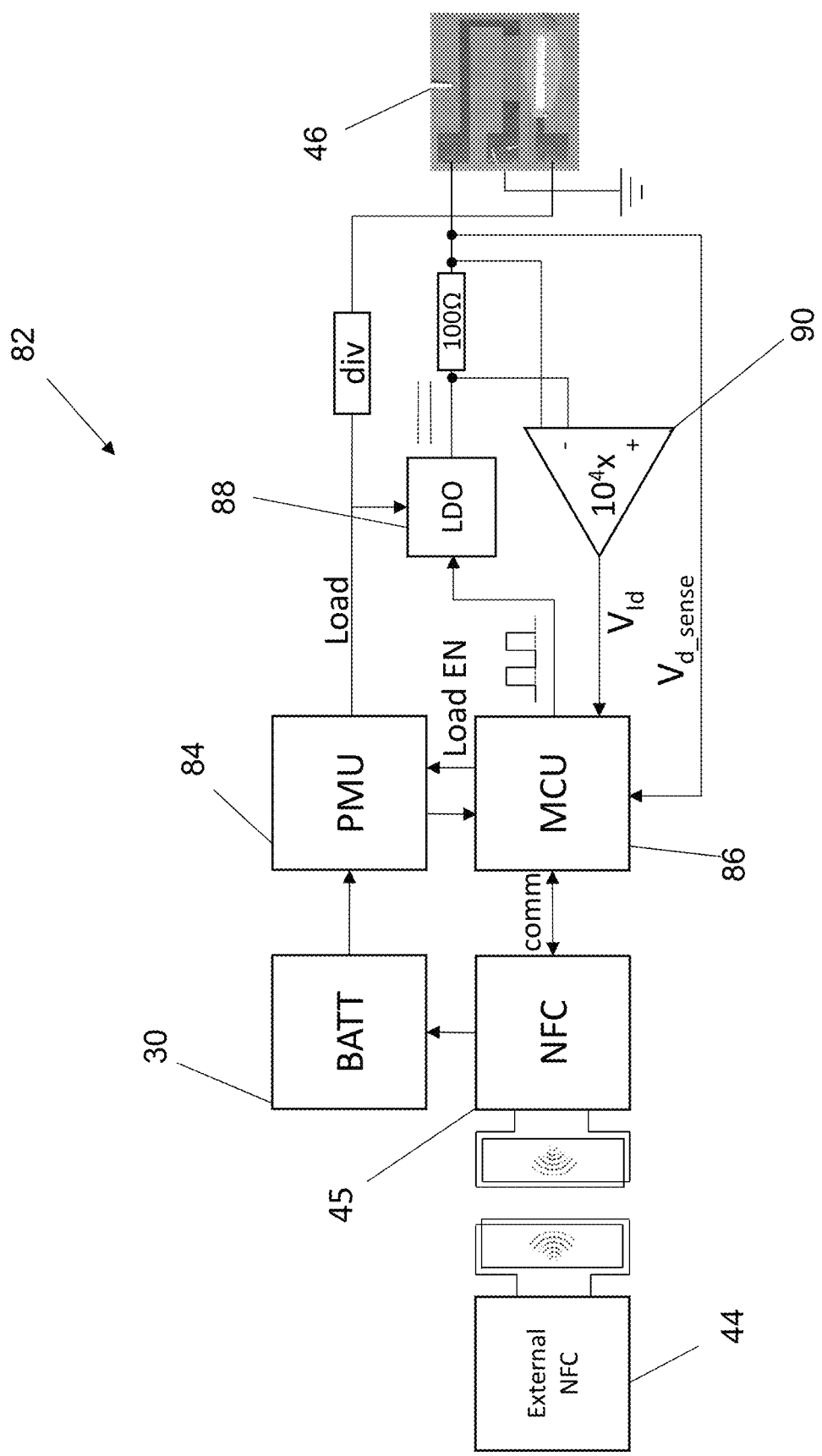
FIG. 4 is a circuit diagram illustrating one contemplated arrangement of elements for the wearable sensor system shown in FIG. 1.

The detection signal generated by the electronic circuit 26 is transmitted to the transceiver 34 via the fourth connection 36. The detection signal is contemplated to be transmitted from the transceiver 34 via a first signal 38 to an external device 44, which is illustrated in FIG. 4, for example.

It is contemplated that the detection signal will be transmitted to the external device 44 wirelessly. The detection signal is contemplated to be transmitted on an intermittent basis so that the detection signal may be plotted as a function of time, for example. The detection signal may be stored in a memory in the external device 44 for subsequent review, consideration, and/or processing, as required and/or as desired. The external device 44 may include a processor to process the detection signal by, for example, displaying the data to a user on a suitable display. Alternatively, the external device 44 may provide the detection signal to other devices for further manipulation, processing, and display.

The external device 44 may be a computer in one example. Alternatively, the external device 44 may be a mobile device, such as a cellular telephone, a smartphone, a smart watch, a tablet, etc., that executes an application for processing the detection signal received from the wearable sensor system 10. It is contemplated that the external device 44 (e.g., the mobile device) will process and display the detection signal at least as a function of time.

The transceiver 34 is contemplated not only to transmit the first signals 38 (outgoing signals), but it is also contemplated to receive second signals 40 (incoming signals). For example, the electronic circuit 26 may include a processor and/or memory that receives input data (the second signals 40) to assist with the operation of the wearable sensor system 10. The second signals 40 may be a software upgrade, for example. For this reason, the transceiver 34 is contemplated both to transmit and receive signals. Naturally, the transceiver 34 may be constructed only to transmit first signals 38 or only to receive second signals 40, as required or as desired, without departing from the scope of the present invention.

The first and second signals 38, 40 are not contemplated to be limited to any particular format. Example formats include, but are not limited to, data formats compatible with Near Field Communication ("NFC"), Bluetooth, WiFi, and the like. As noted herein, the first signals 38 are contemplated to encompass information about the biological molecule(s)/biomarker(s) that are detected by the disposable sensor 20. These signals may be stored, processed, and/or displayed by the external device 44, such as a computer or mobile device. The transmitted first signals 38 may be sent periodically or on demand, as required and/or desired. The second signals 40 are contemplated to provide instructions that are germane to the operation of the wearable sensor system 10.

As illustrated in FIG. 1, the battery 30 is connected to the electronic circuit 26 via the third connection 32. The transceiver 34 is connected to the electronic circuit 26 via the fourth connection 36. The third connection 32 and the fourth connection 36 are contemplated to be wired connections.

As discussed in greater detail in connection, for example, to FIGS. 3 and 4, the disposable sensor 20 is contemplated to detect biological molecules, either directly or indirectly. If the disposable sensor 20 detects the biological molecules indirectly, it is contemplated that the disposable sensor 20 will detect a chemical compound that is associated with and/or generated from the biological molecules. Whether the disposable sensor 20 detects the biological molecules or its associated chemical compound, the disposable sensor 20 is contemplated to detect an ionic material or a polarizable material that is readily attracted to an anode or a cathode, as discussed in greater detail herein.

In connection with the present invention, the term "detect" is intended to encompass several meanings. Detection is intended to refer to the detection of the presence of the biological molecules. Detection also is intended to encompass measurement of the concentration of the biological molecules in the user's perspiration. Still further, detection is intended to encompass measurement of a quantity of the biological molecules in the user's perspiration. Accordingly, the use of the term "detect," and any variants thereof, is not intended to limit the present invention.

It is noted that detection of the concentration of the biological molecules in the user's perspiration depends on a number of variables including, but not limited to, the biomarker being detected, the amount of perspiration generated by the user, the sensitivity of the disposable sensor 20, the amount of voltage and/or current supplied to the disposable sensor 20, etc. Accordingly, the size of the sample of perspiration needed for operation of the disposable sensor 20 and the concentration of the biomarker in the perspiration are not relevant to the present invention. It is noted, however, that the concentration of the biomarker will be in terms of millimoles (mM) or units per milliliter (U/mL) or the like.

The battery 30 is contemplated to be a rechargeable battery. Any type of rechargeable battery may be employed as should be apparent to those skilled in the art. In one contemplated embodiment, the battery 30 may be rechargeable via electromagnetic induction.

Figure 2:
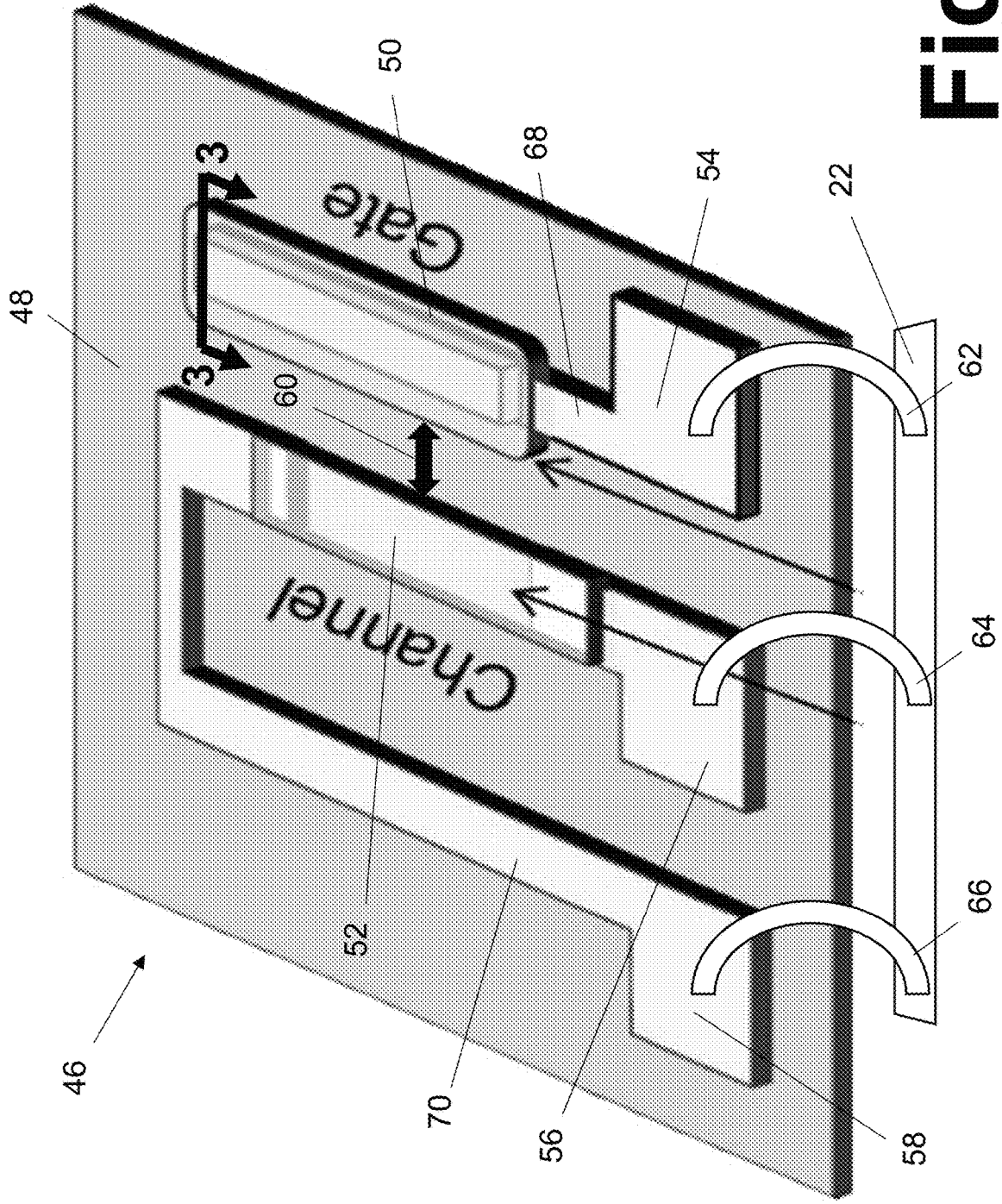
FIG. 2 is a graphical representation of one contemplated embodiment of a disposable sensor useable in the wearable sensor system illustrated in FIG. 1.

FIG. 2 is an illustration of one contemplated embodiment of a disposable sensor 46 according to the present invention. As should be apparent from FIG. 2, the disposable sensor 46 is contemplated to be one specific embodiment of the generic, disposable sensor 20 described above. Accordingly, properties and features of the disposable sensor 20 and the disposable sensor 46 are contemplated to be interchangeable. Moreover, the discussion of the specific embodiment of the disposable sensor 46 is not intended to limit the scope of the present invention.

The disposable sensor 46 is constructed on a substrate 48. The disposable sensor 46 includes a gate electrode 50 and a source drain channel 52 disposed on the substrate 48. In one non-limiting embodiment, the gate electrode 50 may be a functionalized gate electrode and the source drain channel 52 may be an organic semiconductor source-drain channel such as (poly(3,4-ethylenedioxythiophen)/poly(4-styrenesulfonate) (PEDOT:PSS)).

In the illustrated embodiment, the gate electrode 50 is connected to a first pad 54. The source drain channel 52 is connected to a second pad 56 and to a third pad 58. The gate electrode 50 is separated from the source drain electrode 52 by a predetermined distance 60.

In this contemplated embodiment, the gate electrode 50 extends parallel to the source drain electrode 52. However, it is contemplated for alternative embodiments that the gate electrode 50 need not be disposed parallel to the source drain electrode 52.

The electronic circuit 26 connects to the first pad 54 via a first wired connection 62, to the second pad 56 via a second wired connection 64, and to the third pad 58 via a third wired connection 66. As indicated in this illustration, the electronic circuit 26 may be connected to the disposable sensor 46 via the socket 22, which is discussed in connection with FIG. 1.

In the embodiment shown in FIG. 2, the gate electrode 50 is fashioned with a first body 68 that is L-shaped. The source drain electrode 52 is fashioned with a second body 70 that is U-shaped. The disposition of the bodies 68, 70 in this arrangement permits the pads 54, 56, 58 to be aligned along one side of the disposable sensor 46 so that they may more easily be connected to the electronic circuit 26. The shapes of the bodies 68, 70 are not critical to the present invention. Other shapes may be employed without departing from the scope of the present invention.

Figure 3:
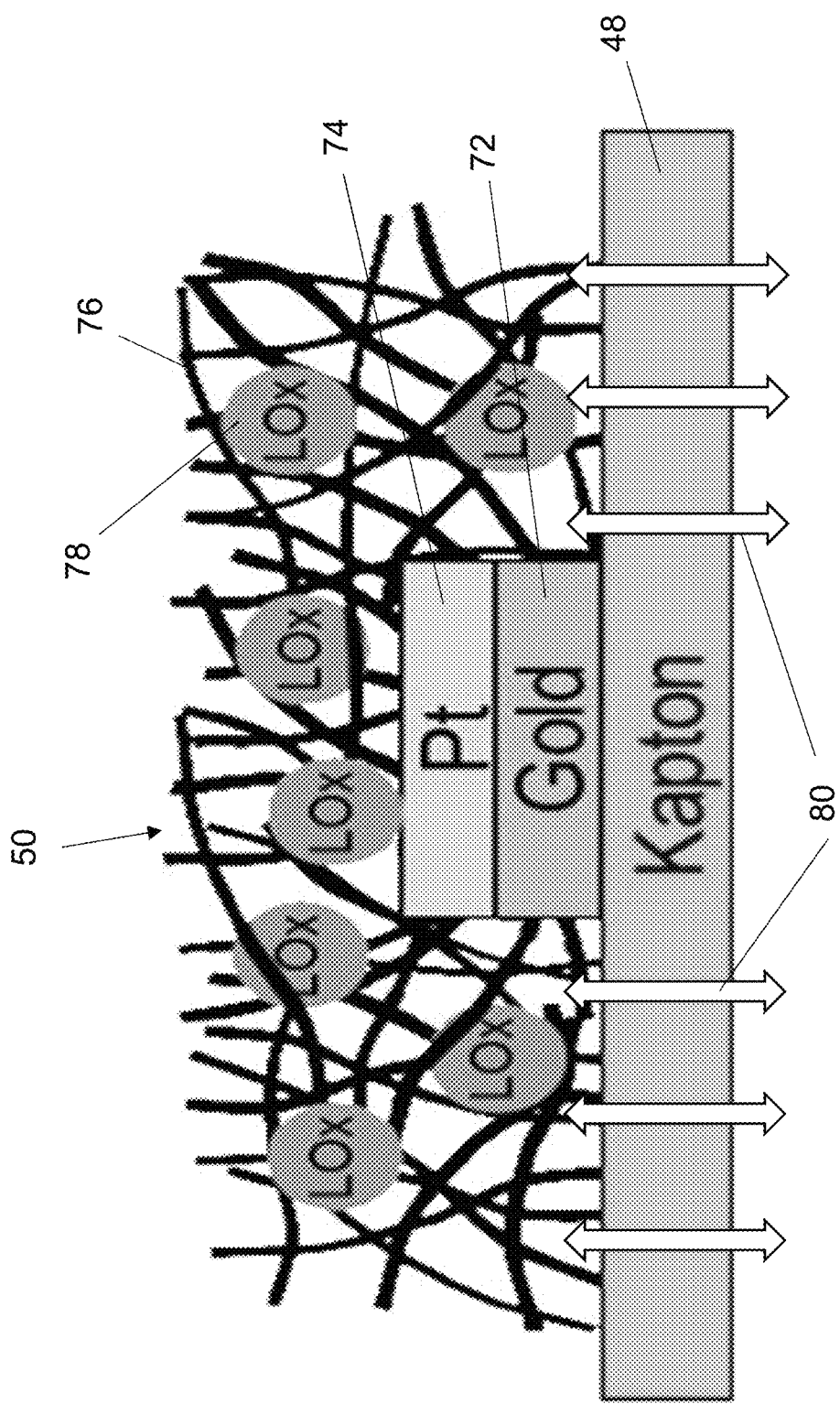
FIG. 3 is a cross-sectional illustration of a portion of the disposable sensor illustrated in FIG. 2, the cross-section being taken along the line 3-3 in FIG. 2.

FIG. 3 is a graphical cross-section, taken along the line 3-3, of the gate electrode 50 illustrated in FIG. 2. The gate electrode 50 is built upon the substrate 48, which may be made from poly(4,4'-oxydiphenylene-pyromellitimide). In this embodiment, the substrate 48 is contemplated to be the flexible patch 12. However, it is also contemplated that the substrate 48 may be disposed on top of the flexible patch 12 without departing from the scope of the present invention.

As illustrated in FIG. 3, the gate electrode 50 comprises a first conductive layer 72 disposed on the substrate 48. In this embodiment, the first conductive layer 72 is gold. However, any suitable alternative, such as copper, platinum, or silver, may be employed without departing from the scope of the present invention. As also shown, a second conductive layer 74 is deposited atop the first conductive layer 72. Here, the second conductive layer 74 is one of platinum or ferric ferrocyanide (also known as "Prussian Blue"). However, as with the first conductive layer 72, any alternative material may be used without departing from the scope of the present invention.

In one further alternative embodiment, only one conductive layer may be employed in place of the two-layer construction that is illustrated in the drawings. A one-layer construction may be made from, for example, gold or platinum.

As also illustrated in FIG. 3, an immobilizing matrix 76 is disposed on the gate electrode 50. An enzyme 78 is immobilized within the immobilizing matrix 76. In the illustrated embodiment, the enzyme 78 is selected to react with the biological molecules in the user's perspiration to produce a chemical compound that is detectible by the disposable sensor 46.

For the illustrated disposable sensor 46, the immobilizing matrix 76 comprises bovine serum albumin and glutaraldehyde. The enzyme 78 is selected to react with one or more of the following biological molecules (e.g., biomarkers): lactate, glucose, glutamate, and acetylcholine. In the illustrated embodiment, the enzyme 78 is lactate oxidase and the biological molecule is lactate.

In the illustrated embodiment, when the user's perspiration is absorbed by the disposable sensor 46, the perspiration interacts with the enzyme 78 that is immobilized in the immobilizing matrix 76. Since the disposable sensor 46 is contemplated to detect lactate in the user's perspiration, the lactate reacts with the lactate oxidase to produce hydrogen peroxide. When a voltage potential is applied to the gate electrode 50 and the source drain electrode 52, the concentration of the hydrogen peroxide, which is the chemical compound associated with the lactate, may be detected by the electronic circuit 26. Specifically, in one non-limiting example, the enzymatic reaction of lactate with lactate oxidase produces hydrogen peroxide. The platinum or Prussian blue catalyzes the reduction of hydrogen peroxide. The gate electrode 50 donates electrons in this process, increasing the gate potential and leading to de-doping of the channel in proportion to the amount of hydrogen peroxide present. The rate of hydrogen peroxide produced is dependent on the rate of the lactate/lactate oxidase reaction, which is in turn dependent on the availability of the lactate oxidase and the concentration of lactate present. Therefore, the sensitivity and range of the disposable sensor 46 is expected to be affected by the amount of lactate oxidase, and the response of the disposable sensor 46 sensor is expected to scale with the amount of lactate present.

As noted, positive voltage applied at the gate electrode 50 drives cations into the PEDOT:PSS channel, effectively de-doping the channel and decreasing the conductivity. In this way, a minute change in the gate potential can be detected as a much larger change in the source-drain current. Furthermore, the degree of de-doping depends on the magnitude of the gate voltage. Therefore, OECTs can be applied as disposable sensors 20 for chemical reactions that result in small changes in the gate potential. As noted herein, the enzymatic reaction between lactate oxidase and lactate may be exploited in one non-limiting example of the present invention.

To facilitate uptake of the user's perspiration so that the perspiration wets the enzyme 78, the disposable sensor 46 is provided with a mechanism 80 that provides access to the enzyme 78 by positioning an electrolyte between the gate electrode 50 and the source drain electrode 52. The electrolyte is contemplated to persist in the predetermined distance 60 between the gate electrode 50 and the source drain electrode 52. The electrolyte fluidically connects the gate electrode 50 to the source drain electrode 52.

The electrolyte may be of any type known to those skilled in the art. It is contemplated, for example, that the electrolyte at least partially comprises the perspiration of the user. The electrolyte may be a salt solution, for example. Still further, the electrolyte may be any electrolyte solution containing mobile ions.

In FIG. 3, the mechanism 80 is contemplated to be an array of microneedles that provide access to the electrolyte. Any other arrangement may be employed without departing from the scope of the present invention. For example, the mechanism 80 may be a material that facilitates wicking of perspiration from the skin of the user to the disposable sensor 46. For another example, the mechanism 80 may be direct contact of the sensor to the skin of the user, by positioning the sensor on the underside 16 of the flexible patch 12.

FIG. 4 provides an electronic and power schematic 82 for one contemplated embodiment of the wearable sensor system 10 according to the present invention.

The electronic schematic 82 of the wearable sensor system 10 includes a disposable sensor 46, a battery 30 (e.g., EFL700A39, ST Microelectronics), a power management unit 84 (e.g., TPS82740A, Texas Instruments), a microcontroller unit 86 (e.g., ATtiny24A, Atmel), an inverting low-dropout voltage regulator 88, and an amplifier 90. The electronic schematic 82 of the wearable sensor system 10 illustrated in FIG. 4 is merely exemplary of one contemplated embodiment of the present invention. As should be apparent to those skilled in the art, other configurations may be employed without departing from the scope of the present invention.

The electronic schematic 82 of the wearable sensor system 10 employs a lactate sensor as the disposable sensor 46. The disposable sensor 46 collects sensor data (e.g., first data 38) as well as exfiltrating the sensor data to, for example, an application running on a mobile device (e.g., the external device 44). The external device 44 and the microcontroller unit 86 communicate via an NFC interface 45 (e.g., AS3955, AMS), which is illustrated as a part of the external device 44. The microcontroller unit 86 controls the state of the wearable sensor system 10 (e.g., sleep, sensing, or communications mode) based on commands received, via the NFC interface 45, from the external device 44, for example. The microcontroller unit 86 also handles the transfer of data from the onboard non-volatile memory through the NFC interface 45. The NFC interface 45 handles the protocol for communication with the application running on the mobile device (e.g., the external device 44) and concurrently harvests power from the communication signal to charge the onboard battery 30 through an internal voltage regulator contained inside the NFC interface 45 illustrated in FIG. 4 (e.g., the NFC charges battery 30 which drives power management unit 84). In one embodiment, the type of battery 30 allows for the same battery output and input and does not require a specialized charging circuit to manage current in and current out.

Sensing by the disposable sensor 46 (e.g., the OECT) requires measurement of a current (I) under the conditions of a bi-polar voltage between the source drain electrode 52 and the gate electrode 50. For this reason, the electronic circuit 82 of the wearable sensor system 10 contains the inverting low-dropout voltage regulator 88 to supply a negative voltage, which is then regulated down by the microcontroller unit 86 to supply the desired voltage at the source drain electrode 52. A current sense amplifier 90 is placed in line from the amplifier output to the source drain electrode 52 and the output of the amplifier 90 is read and recorded to a non-volatile memory by the microcontroller unit 86.

The above description is meant to be exemplary only, and those skilled in the art will recognize that changes may be made to the embodiments without departing from the scope of the present invention. Variations and equivalents to one or more aspects of the invention may employed without departing from the teachings of the present disclosure. Moreover, the present disclosure may be embodied in other specific forms without departing from the subject matter of the claims. Modifications, variations, and equivalents that fall within the scope of the present invention, as should be apparent to those skilled in the art, are intended to fall within the scope of the claims. Also, the scope of the claims is not intended to be limited by the embodiments set forth herein. Instead, the scope of the claims is intended to be given the broadest interpretation consistent with the description as a whole.

What is claimed is:

1. A wearable sensor system, comprising:
a flexible patch;
a socket;
an electronic circuit disposed on the flexible patch and connected to the socket;
a disposable sensor disposed on the flexible patch and removably connected to the electronic circuit via the socket, wherein the disposable sensor detects a chemical compound,
the electronic circuit generates a detection signal commensurate with the chemical compound detected by the disposable sensor, and
the disposable sensor is removably plugged into the socket, thereby permitting replacement of the disposable sensor upon satisfaction of a predetermined condition;
a battery disposed on the flexible patch and connected to the electronic circuit to power the electronic circuit; and
a transceiver connected to the electronic circuit, wherein the transceiver transmits the detection signal;
wherein the disposable sensor comprises:
a flexible substrate;
a gate electrode built upon the flexible substrate and connected to a first connection pad, wherein the flexible substrate is configured to permit biological molecules in perspiration of a user to pass through the flexible substrate at the gate electrode to react and produce the chemical compound for detection, wherein the gate electrode comprises a first portion of a first conductive layer disposed on the flexible substrate and a second conductive layer disposed atop the first portion of the first conductive layer, wherein an immobilizing matrix having a consumable enzyme immobilized within the immobilizing matrix is disposed on the flexible substrate and encapsulates the gate electrode where the second conductive layer is disposed atop the portion of the first conductive layer such that the biological molecules that pass through the flexible substrate and enter the immobilizing matrix to directly interact with the consumable enzyme and the second conductive layer disposed within the immobilizing matrix, wherein the consumable enzyme reacts with the biological molecules to produce the chemical compound detectible by the disposable sensor, wherein second conductive layer of the gate electrode is entirely disposed within the immobilizing matrix and a second portion of the first conductive layer extends out of the immobilizing matrix and widens to form the first connection pad; and
a source drain electrode disposed on the flexible substrate, the source drain electrode being connected to a second connection pad and a third connection pad;
wherein the first connection pad, the second connection pad, and the third connection pad are configured to make a removable connection between the disposable sensor and the electronic circuit via the socket;
wherein the source drain electrode is disposed on a U-shaped body that extends from the second connection pad to the third connection pad, the U-shaped body comprising a proximal leg and a distal leg, the proximal leg being closer to the gate electrode than the distal leg;
wherein the proximal leg comprises an organic semiconductor and the organic semiconductor is disposed only along a portion of the proximal leg that is parallel to the second conductive layer of the gate electrode along an extended length and separated by a predetermined distance.

2. The wearable sensor system of claim 1, further comprising an adhesive disposed on the flexible patch to affix the flexible patch to a skin of the user.

3. The wearable sensor system of claim 1, wherein the disposable sensor comprises at least one organic electrochemical transistor.

4. The wearable sensor system of claim 1, wherein:
the first conductive layer is gold, and
the second conductive layer is at least one of platinum or ferric ferrocyanide.

5. The wearable sensor system of claim 1, wherein the consumable enzyme is configured to react with the biological molecules, the biological molecules comprising lactate, glucose, glutamate, or acetylcholine.

6. The wearable sensor system of claim 1, wherein the consumable enzyme is lactate oxidase and the biological molecules are lactate.

7. The wearable sensor system of claim 1, wherein the immobilizing matrix comprises bovine serum albumin and glutaraldehyde.

8. The wearable sensor system of claim 1, further comprising:
a transport mechanism providing access to an electrolyte positioned between the gate electrode and the source drain electrode to fluidically connect the gate electrode to the source drain electrode, wherein the electrolyte comprises the perspiration of the user and an electrolyte containing mobile ions.

9. The wearable sensor system of claim 8, further comprising:
an array of microneedles as the transport mechanism providing access to the electrolyte.

10. The wearable sensor system of claim 1, wherein the disposable sensor detects a concentration of the chemical compound at a periodic interval.

11. The wearable sensor system of claim 1, wherein the chemical compound is hydrogen peroxide.

12. The wearable sensor system of claim 1, wherein the disposable sensor detects a concentration of the chemical compound; and
wherein the detection signal comprises the concentration of the chemical compound.

13. The wearable sensor system of claim 1, wherein the transceiver transmits the detection signal wirelessly.

14. The wearable sensor system of claim 1, wherein the first connection pad, the second connection pad, and the third connection pad are aligned along a common side of the substrate to facilitate the removable connection with the electronic circuit via the socket.

15. The wearable sensor system of claim 1, wherein the flexible substrate comprises poly (4,4'-oxydiphenylene-pyromellitimide).

16. The wearable sensor system of claim 1, wherein the gate electrode and the source drain electrode are disposed on a first side of the flexible substrate; and
wherein a second side of the flexible substrate, that is opposite the first side, is configured to be applied to a skin of the user.

* * * * *